US007713533B2

(12) United States Patent
Svanborg

(10) Patent No.: US 7,713,533 B2
(45) Date of Patent: *May 11, 2010

(54) ACTIVE COMPLEX OF α-LACTALBUMIN (HAMLET) AND COFACTOR

(75) Inventor: Catharina Svanborg, Lund (SE)

(73) Assignee: NYA HAMLET Pharma AB, Copenhagen Ø (DK)

( * ) Notice: Subject to any disclaimer, the term of this patent is extended or adjusted under 35 U.S.C. 154(b) by 18 days.

This patent is subject to a terminal disclaimer.

(21) Appl. No.: 11/892,499

(22) Filed: Aug. 23, 2007

(65) Prior Publication Data

US 2008/0167233 A1 Jul. 10, 2008

Related U.S. Application Data

(62) Division of application No. 10/513,740, filed as application No. PCT/IB03/02366 on May 8, 2003, now Pat. No. 7,270,822.

(30) Foreign Application Priority Data

May 8, 2002 (GB) .................................. 0210464.4

(51) Int. Cl.
*A61K 38/00* (2006.01)
*C07C 53/00* (2006.01)
(52) U.S. Cl. ..................... 424/195.11; 514/12; 530/300; 554/1
(58) Field of Classification Search ........................ None
See application file for complete search history.

(56) References Cited

U.S. PATENT DOCUMENTS

| 4,348,376 | A | 9/1982 | Goldenberg |
| 5,614,191 | A | 3/1997 | Puri et al. |
| 6,159,748 | A | 12/2000 | Hechinger |
| 6,455,673 | B1 | 9/2002 | Collier |
| 7,270,822 | B2 * | 9/2007 | Svanborg ............... 424/195.11 |
| 2001/0044416 | A1 | 11/2001 | McCluskie |
| 2005/0085416 | A1 | 4/2005 | Svanborg et al. |
| 2006/0074017 | A1 | 4/2006 | Svanborg |
| 2008/0039381 | A1* | 2/2008 | Svanborg ..................... 514/12 |

FOREIGN PATENT DOCUMENTS

| FR | 2 671 697 | 7/1992 |
| WO | WO 96/04929 | 2/1996 |
| WO | WO 99/26979 | 6/1999 |
| WO | WO 99/27967 | 6/1999 |
| WO | 01 72784 A | 10/2001 |
| WO | WO 01/77137 | 10/2001 |
| WO | WO 03/074547 A2 | 9/2003 |

OTHER PUBLICATIONS

Svanborg et al, Advances in Cancer Research, 2003, vol. 88, pp. 1-29.
Svensson et al, PNAS, Apr. 11, 2000, vol. 97, No. 8, pp. 4221-4226.
Kohler et al, European Journal of Biochemistry, Jan. 2001, vol. 268, No. 1, pp. 186-191.
Polverino de Laureto Patrizia et al, Proteins, Nov. 15, 2002, vol. 49, No. 3, pp. 385-397.
Svensson Malin et al, Advances in Experimental Medicine and Biology, 2002, vol. 503, pp. 125-132.
Schwartz et al, Immunology Today, 1993, vol. 14, No. 12, pp. 582-590.
McConkey et al, Molec. Aspects Med., 1996, vol. 17, pp. 1-110.
Kerr et al, Cancer, 1994, vol. 73, No. 8, pp. 2013-2026.
Arends et al, American Journal of Pathology, 1990, vol. 136, pp. 593-608.
Zhivotovsky et al, FEBS Letters, 1994, vol. 351, pp. 150-154.
Zhivotovsky et al, Experimental Cell Research, 1995, vol. 221, pp. 404-412.
Kumar, TIBS, 1995, vol. 20, pp. 198-202.
Zheng et al, Nature, 1995, vol. 377, pp. 348-351.
Declercq et al, Cytokine, 1995, vol. 7, No. 7, pp. 701-709.
Griffith et al, Science, 1995, vol. 270, pp. 1189-1192.
Jans et al, Physiological Reviews, 1996, vol. 76, No. 3, pp. 651-685.
Gorlich et al, Science, 1996, vol. 271, pp. 1513-1518.
Yoneda, J. Biochem., 1997, vol. 121, pp. 811-817.
Yang et al, Molecular and Cellular Biology, 1994, vol. 14, No. 8, pp. 5088-5098.
Heine et al, S. Nutr., 1991, vol. 121, pp. 277-283.
Sheridan et al, Science, 1997, vol. 277, pp. 818-821.
Pan et al, Science, 1997, vol. 277, pp. 815-818.
Adam et al, The Journal of Cell Biology, 1990, vol. 111, pp. 807-816.
Garcia-Bustos et al, Biochem. Biophys. Acta, 1991, vol. 1071, pp. 83-101.
Ren et al, The Journal of Biological Chemistry, 1992, vol. 268, No. 26, pp. 19292-19298.
Kuwajima et al, FASEB J., 1996, vol. 10, pp. 102-109.
Alexandrescu et al, Biochemistry, 1993, No. 32, pp. 1707-1708.
Kabara et al, Antimicrobial Agents and Chemotherapy, 1972, vol. 2, No. 1, pp. 23-28.
Gill et al, Science, 1983, vol. 221, pp. 1290-1293.
Davis et al, The Lancet, 1988, pp. 365-368.
Siskind et al, American Journal of Epidemiology, 1989, vol. 130, No. 2, pp. 229-236.
Newcomb et al, The New England Journal of Medicine, 1994, vol. 330, pp. 81-87.
Sander et al, Immunological Review, 1991, No. 119, pp. 65-93.
Graham, Isolation of Subcellular Organelles and Membranes, p. 161-182 in D. Rickwood, ed., Centrifugation, a practical approach, 2$^{nd}$ ed., IRL Press, Washington, D.C.
Hakansson et al, Experimental Cell Research, 1999, vol. 246, pp. 451-460.
Hakansson et al, Proc. Nat'l. Acad. Sci., 1995, vol. 92, pp. 8064-8068.
Ming, Magnetic Resonance in Chemistry, 1993, vol. 31, pp. S104-S109.
Signore et al, European Journal of Endocrinology, 1994, vol. 131, pp. 431-347.

(Continued)

*Primary Examiner*—Anand U Desai
(74) *Attorney, Agent, or Firm*—Nixon & Vanderhye P.C.

(57) ABSTRACT

The use of a biologically active complex of α-lactalbumin, selected from HAMLET (human α-lactalbumin made lethal to tumour cells) or a biologically active modification thereof, or a biologically active fragment of either of these, in the preparation of a medicament for use in the treatment of papilloma, such as cutaneous papillomas.

16 Claims, No Drawings

OTHER PUBLICATIONS

Blair et al, Journal of Immunological Methods, 1983, vol. 59, pp. 129-143.
Johnstone et al, Immunochemistry in Practice 2nd Edition, Blackwell Scientific Publications Oxford, 1987, pp. 113-130.
Goers, Immunochemical Techniques Laboratory Manual, Academic Press, San Diego 1993, pp. 69-79.
Jain, Scientific American, vol. 271, pp. 58-65.
Zeisel et al, J. Nutr. 1986, vol. 116, pp. 50-58.
Kronman et al, Biochemistry, 1965, vol. 4, No. 3, pp. 518-525.
Dolgikh et al, FEBS Letters, 1981, vol. 136, No. 2, pp. 311-315.
Dolgikh et al, FEBS Letters, 1984, vol. 165, No. 1, pp. 88-92.
Ohgushi et al, FEBS Letters, 1983, vol. 164, No. 1, pp. 21-24.
Pfeil, Biochimica et Biophysica Acta, 1987, pp. 114-116.
Kuwajima, The FASEB Journal, vol. 10, pp. 102-109.
Jegouic et al, J. Agric. Food Chem. 1997, No. 45, pp. 19-22.
Schulman et al, J. Mol. Biol., 1995, vol. 253, pp. 651-657.
Bitman et al, Journal of Pediatric Gastroenterology and Nutrition, 1983, vol. 2, No. 3, pp. 521-524.
Hall et al, Biochem. J. 1987, vol. 242, pp. 735-742.
Davies et al, Ann. Hum. Genet. 1987, vol. 51, pp. 183-188.
Peng et al, Biochemistry, 1994, vol. 33, pp. 2136-2141.
Robinett et al, The Journal of Cell Biology, 1996, vol. 135, No. 6, pp. 1685-1700.
Svensson et al, The Journal of Biological Chemistry, 1999, vol. 274, No. 10, pp. 6388-6396.
Tatsumi et al, Biosci. Biotechnol. Biochem., 1999, vol. 63, No. 7, pp. 1285-1290.
Freeman et al, Free Radical Biology & Medicine, 1999, vol. 26, Nos. 5/6, pp. 737-745.
Hakansson et al, Molecular Microbiology, 2000, vol. 35, No. 3, pp. 589-600.
Database BIOSIS Biosciences Information Service, Philadelphia, PA, US, Oct. 2001, Sergei et al; "Mutating Aspartate in the Calcium-Binding Site of Alpha-Lactalbumin: Effects on the Protein Stability and Cation Binding"; Database Accession No. PREV200200099182m XO002250707 & Protein Engineering, vol. 14, No. 10, Oct. 2001, pp. 785-789.
Watanabe M, (J. Vet. Med. Sci. 62 (11): 1217-1219 (2000).
Permyakov et al, "Mutating aspartate in the calcium-binding site of α-lactalbumin: effects on the protein stability and cation binding", Protein Engineering vol. 14, No. 10, pp. 785-789, 2001.
Svensson et al, "Lipids as cofactors in protein folding: Stereo-specific lipid-protein interactions are required to form HAMLET (human alpha-lactalbumin made lethal to tumor cells)", Protein Science 12:2805-2814 (2003).
Pending claims in U.S. Appl. No. 10/590,938, filed Jun. 26, 2009.
Pending claims in U.S. Appl. No. 10/506,903, filed Nov. 11, 2008.

* cited by examiner

SEQUENCE LISTING

<160> NUMBER OF SEQ ID NOS: 7

<210> SEQ ID NO 1
<211> LENGTH: 123
<212> TYPE: PRT
<213> ORGANISM: homo sapiens

<400> SEQUENCE: 1

```
Lys Gln Phe Thr Lys Cys Glu Leu Ser Gln Leu Leu Lys Asp Ile Asp
1               5                   10                  15

Gly Tyr Gly Gly Ile Ala Leu Pro Glu Leu Ile Cys Thr Met Phe His
            20                  25                  30

Thr Ser Gly Tyr Asp Thr Gln Ala Ile Val Glu Asn Asn Glu Ser Thr
        35                  40                  45

Glu Tyr Gly Leu Phe Gln Ile Ser Asn Lys Leu Trp Cys Lys Ser Ser
    50                  55                  60

Gln Val Pro Gln Ser Arg Asn Ile Cys Asp Ile Ser Cys Asp Lys Phe
65                  70                  75                  80

Leu Asp Asp Asp Ile Thr Asp Asp Ile Met Cys Ala Lys Lys Ile Leu
                85                  90                  95

Asp Ile Lys Gly Ile Asp Tyr Trp Leu Ala His Lys Ala Leu Cys Thr
            100                 105                 110

Glu Lys Leu Glu Gln Trp Leu Cys Glu Lys Leu
        115                 120
```

<210> SEQ ID NO 2
<211> LENGTH: 123
<212> TYPE: PRT
<213> ORGANISM: Bos taurus

<400> SEQUENCE: 2

```
Glu Gln Leu Thr Lys Cys Glu Val Phe Arg Glu Leu Lys Asp Leu Lys
1               5                   10                  15

Gly Tyr Gly Gly Val Ser Leu Pro Glu Trp Val Cys Thr Thr Phe His
            20                  25                  30

Thr Ser Gly Tyr Asp Thr Gln Ala Ile Val Gln Asn Asn Asp Ser Thr
        35                  40                  45

Glu Tyr Gly Leu Phe Gln Ile Asn Asn Lys Ile Trp Cys Lys Asp Asp
    50                  55                  60
```

Gln Asn Pro His Ser Ser Asn Ile Cys Asn Ile Ser Cys Asp Lys Phe
65                  70                  75                  80

Leu Asp Asp Asp Leu Thr Asp Ile Met Cys Val Lys Lys Ile Leu
                85                  90                  95

Asp Lys Val Gly Ile Asn Tyr Trp Leu Ala His Lys Ala Leu Cys Ser
            100                 105                 110

Glu Lys Leu Asp Gln Trp Leu Cys Glu Lys Leu
            115                 120

<210> SEQ ID NO 3
<211> LENGTH: 123
<212> TYPE: PRT
<213> ORGANISM: Ovis aries

<400> SEQUENCE: 3

Glu Gln Leu Thr Lys Cys Glu Val Phe Gln Glu Leu Lys Asp Leu Lys
1               5                   10                  15

Asp Tyr Gly Gly Val Ser Leu Pro Glu Trp Val Cys Thr Ala Phe His
            20                  25                  30

Thr Ser Gly Tyr Asp Thr Gln Ala Ile Val Gln Asn Asn Asp Ser Thr
        35                  40                  45

Glu Tyr Gly Leu Phe Gln Ile Asn Asn Lys Ile Trp Cys Lys Asp Asp
50                  55                  60

Gln Asn Pro His Ser Arg Asn Ile Cys Asn Ile Ser Cys Asp Lys Phe
65                  70                  75                  80

Leu Asp Asp Asp Leu Thr Asp Ile Met Cys Val Lys Lys Ile Leu
                85                  90                  95

Asp Lys Val Gly Ile Asn Tyr Trp Leu Ala His Lys Ala Leu Cys Ser
            100                 105                 110

Glu Lys Leu Asp Gln Trp Leu Cys Glu Lys Leu
            115                 120

<210> SEQ ID NO 4
<211> LENGTH: 123
<212> TYPE: PRT
<213> ORGANISM: Capra hircus

<400> SEQUENCE: 4

Glu Gln Leu Thr Lys Cys Glu Val Phe Gln Lys Leu Lys Asp Leu Lys
1               5                   10                  15

Asp Tyr Gly Gly Val Ser Leu Pro Glu Trp Val Cys Thr Ala Phe His
            20                  25                  30

Thr Ser Gly Tyr Asp Thr Gln Ala Ile Val Gln Asn Asn Asp Ser Thr
        35                  40                  45

Glu Tyr Gly Leu Phe Gln Ile Asn Asn Lys Ile Trp Cys Lys Asp Asp
50                  55                  60

Gln Asn Pro His Ser Arg Asn Ile Cys Asn Ile Ser Cys Asp Lys Phe
65                  70                  75                  80

Leu Asp Asp Asp Leu Thr Asp Ile Val Cys Ala Lys Lys Ile Leu
                85                  90                  95

Asp Lys Val Gly Ile Asn Tyr Trp Leu Ala His Lys Ala Leu Cys Ser
            100                 105                 110

Glu Lys Leu Asp Gln Trp Leu Cys Glu Lys Leu
            115                 120

<210> SEQ ID NO 5
<211> LENGTH: 123

```
<212> TYPE: PRT
<213> ORGANISM: Artificial Sequence
<220> FEATURE:
<223> OTHER INFORMATION: D87A mutant

<400> SEQUENCE: 5
```

Glu Gln Leu Thr Lys Cys Glu Val Phe Arg Glu Leu Lys Asp Leu Lys
1               5                   10                  15

Gly Tyr Gly Gly Val Ser Leu Pro Glu Trp Val Cys Thr Thr Phe His
            20                  25                  30

Thr Ser Gly Tyr Asp Thr Gln Ala Ile Val Gln Asn Asn Asp Ser Thr
        35                  40                  45

Glu Tyr Gly Leu Phe Gln Ile Asn Asn Lys Ile Trp Cys Lys Asp Asp
    50                  55                  60

Gln Asn Pro His Ser Ser Asn Ile Cys Asn Ile Ser Cys Asp Lys Phe
65                  70                  75                  80

Leu Asp Asp Asp Leu Thr Ala Asp Ile Met Cys Val Lys Lys Ile Leu
                85                  90                  95

Asp Lys Val Gly Ile Asn Tyr Trp Leu Ala His Lys Ala Leu Cys Ser
                100                 105                 110

Glu Lys Leu Asp Gln Trp Leu Cys Glu Lys Leu
            115                 120

```
<210> SEQ ID NO 6
<211> LENGTH: 123
<212> TYPE: PRT
<213> ORGANISM: Artificial Sequence
<220> FEATURE:
<223> OTHER INFORMATION: D87N mutant

<400> SEQUENCE: 6
```

Glu Gln Leu Thr Lys Cys Glu Val Phe Arg Glu Leu Lys Asp Leu Lys
1               5                   10                  15

Gly Tyr Gly Gly Val Ser Leu Pro Glu Trp Val Cys Thr Thr Phe His
            20                  25                  30

Thr Ser Gly Tyr Asp Thr Gln Ala Ile Val Gln Asn Asn Asp Ser Thr
        35                  40                  45

Glu Tyr Gly Leu Phe Gln Ile Asn Asn Lys Ile Trp Cys Lys Asp Asp
    50                  55                  60

Gln Asn Pro His Ser Ser Asn Ile Cys Asn Ile Ser Cys Asp Lys Phe
65                  70                  75                  80

Leu Asp Asp Asp Leu Thr Asn Asp Ile Met Cys Val Lys Lys Ile Leu
                85                  90                  95

Asp Lys Val Gly Ile Asn Tyr Trp Leu Ala His Lys Ala Leu Cys Ser
                100                 105                 110

Glu Lys Leu Asp Gln Trp Leu Cys Glu Lys Leu
            115                 120

```
<210> SEQ ID NO 7
<211> LENGTH: 123
<212> TYPE: PRT
<213> ORGANISM: Artificial Sequence
<220> FEATURE:
<223> OTHER INFORMATION: S70R mutant

<400> SEQUENCE: 7
```

Glu Gln Leu Thr Lys Cys Glu Val Phe Arg Glu Leu Lys Asp Leu Lys
1               5                   10                  15

Gly Tyr Gly Gly Val Ser Leu Pro Glu Trp Val Cys Thr Thr Phe His

```
                    20                  25                  30
Thr Ser Gly Tyr Asp Thr Gln Ala Ile Val Gln Asn Asn Asp Ser Thr
        35                  40                  45

Glu Tyr Gly Leu Phe Gln Ile Asn Asn Lys Ile Trp Cys Lys Asp Asp
        50                  55                  60

Gln Asn Pro His Ser Arg Asn Ile Cys Asn Ile Ser Cys Asp Lys Phe
65                  70                  75                  80

Leu Asp Asp Asp Leu Thr Asp Asp Ile Met Cys Val Lys Lys Ile Leu
                85                  90                  95

Asp Lys Val Gly Ile Asn Tyr Trp Leu Ala His Lys Ala Leu Cys Ser
            100                 105                 110

Glu Lys Leu Asp Gln Trp Leu Cys Glu Lys Leu
        115                 120
```

ACTIVE COMPLEX OF α-LACTALBUMIN (HAMLET) AND COFACTOR

This application is a divisional of application Ser. No. 10/513,740, filed May 13, 2005 (issued as U.S. Pat. No. 7,270,822 on Sep. 18, 2007), which is a U.S. National Phase of International Application No. PCT/IB03/02366, filed May 8, 2003, which designated the U.S. and claims benefit of GB 0210464.4, filed May 8, 2002, the entire contents of each of which is hereby incorporated by reference in this application.

The present invention relates to a method of treatment of papilloma, and to the use of biologically active complexes in the preparation of medicaments for the treatment of papilloma such as cutaneous papillomas or warts.

Papillomas are tumours of the skin and mucosal surfaces, formed by human papilloma virus (HPV) transformed keratinocytes. Most of the skin lesions remain benign, but the mucosal lesions are pre-malignant and cervical cancer is an important sequel of HPV infection, with >750,000 cases reported annually. Most of the cervical cancers contain a restricted number of HPV types (HPV 16 and 18) but cutaneous papillomas lack this virus specificity. They are caused by one or more of about 130 different HPV types and include plantar, common and flat warts. Immuno-suppressed patients run an increased risk to develop papillomas, and may carry multiple HPV types at high frequency. Current treatments include cryotherapy, curettage, cautery, topical virucidal agents, laser, anti-mitotic agents and immuno-activators. HPV vaccine are being developed for cervical papillomas, but they are not yet in use.

HAMLET (human α-lactalbumin made lethal to tumour cells) (formerly known as MAL) is an active folding variant of alpha-lactalbumin (also represented as α-lactalbumin) that induces apoptosis in transformed cells but spares healthy differentiated cells [(M. Svensson, et al., (2000) *Proc Natl Acad Sci* USA, 97, 4221-6). HAMLET has been shown to bind to the surface of tumour cells, to translocate into the cytoplasm and to accumulate in cell nuclei, where it causes DNA fragmentation (M. Svensson, et al., (2000) *Proc Natl Acad Sci* USA, 97, 4221-6). Biologically active complexes of this type, obtained from milk and particularly human milk, together with their use as antibacterial agents is described for example in EP-0776214.

The applicants have found that HAMLET and complexes of this type are useful in the treatment of papilloma and particularly cutaneous papillomas.

According to the present invention, there is provided the use of a biologically active complex of α-lactalbumin, selected from HAMLET or a biologically active modification thereof, or a biologically active fragment of either of these, in the preparation of a medicament for use in the treatment of papilloma.

Papilloma which may be treated using the medicament include papilloma of any of the serotypes listed above. These include cutaneous papillomas and genital papillomas.

As used herein, the term "HAMLET" refers to a biologically active complex of α-lactalbumin, which is either obtainable by isolation from casein fractions of milk which have been precipitated at pH 4.6, by a combination of anion exchange and gel chromatography as described for example in EP-A-0776214, or by subjecting α-lactalbumin to ion exchange chromatography in the presence of a cofactor from human milk casein, characterized as C18:1 fatty acid as described in WO99/26979.

The α-lactalbumin may be from various mammalian sources including human, bovine, sheep and goat milk, but is preferably human or bovine, and most preferably human. Recombinant forms of the protein may also be employed.

It has also been found that other reagents and specifically lipids such as oleic acid, are useful in the conversion of human α-lactalbumin to HAMLET. In particular, it has been reported previously that oleic acid (C18:1:9cis) is required for HAMLET production (M. Svensson, et al., (2000) *Proc Natl Acad Sci* USA, 97, 4221-6). More recently, it has been found that other fatty acids may act as co-factors in a similar way. Optimal cofactors for the conversion of α-lactalbumin to HAMLET are C18:1 fatty acids with a double bond in the cis conformation at position 9 or 11.

α-Lactalbumin is a 14.2 kDa globular protein with four α-helices (residues 1-34, 86-123) and an anti-parallel β-sheet (residues 38-82), linked by four disulphide bonds (61-77; 73-91; 28-111 and 6-120) (K. R. Acharya, et al., (1991) *J Mol Biol,* 221, 571-81). The native conformation of α-lactalbumin is defined by a high affinity $Ca^{2+}$ binding site, co-ordinated by the side chain carboxylates of Asp82, Asp87 and Asp88, the carbonyl oxygens of Lys79 and Asp84, and two water molecules (K. R. Acharya, et al., (1991) *J Mol Biol,* 221, 571-81). The protein adopts the so called apo-conformation found in HAMLET when exposed to low pH, or in the presence of chelators, that release the strongly bound $Ca^{2+}$ ion (D. A. Dolgikh, et al., (1981) *FEBS Lett,* 136, 311-5; K. Kuwajima, (1996) *Faseb J,* 10, 102-09).

In order to form biologically active complexes, α-lactalbumin generally requires both a conformational or folding change as well as the presence of a lipid cofactor. The conformational change is suitably effected by removing calcium ions from α-lactalbumin. In a preferred embodiment, this is suitably facilitated using a variant of α-lactalbumin which does not have a functional calcium binding site.

Biologically active complexes which contain such variants are encompassed by the term "modifications" of HAMLET as used herein. However, the applicants have found that, once formed, the presence of a functional calcium binding site, and/or the presence of calcium, does not affect stability or the biological activity of the complex. Biologically active complexes have been found to retain affinity for calcium, without loss of activity. Therefore complex of the invention may further comprise calcium ions.

Thus in particular, the invention uses a biologically active complex comprising alpha-lactalbumin or a variant of alpha-lactalbumin which is in the apo folding state, or a fragment of either of any of these, and a cofactor which stabilises the complex in a biologically active form, provided that any fragment of alpha-lactalbumin or a variant thereof comprises a region corresponding to the region of α-lactalbumin which forms the interface between the alpha and beta domains.

Suitably the cofactor is a cis C18:1:9 or C18:1:11 fatty acid or a different fatty acid with a similar configuration.

In a particular convenient embodiment, the biologically active complex used in the invention comprises (i) a cis C18:1:9 or C18:1:11 fatty acid or a different fatty acid with a similar configuration; and (ii) α-lactalbumin from which calcium ions have been removed, or a variant of α-lactalbumin from which calcium ions have been released or which does not have a functional calcium binding site; or a fragment of either of any of these, provided that any fragment comprises a region corresponding to the region of α-lactalbumin which forms the interface between the alpha and beta domains.

As used herein the expression "variant" refers to polypeptides or proteins which are homologous to the basic protein, which is suitably human or bovine α-lactalbumin, but which differ from the base sequence from which they are derived in that one or more amino acids within the sequence are substituted for other amino acids. Amino acid substitutions may be regarded as "conservative" where an amino acid is replaced with a different amino acid with broadly similar properties. Non-conservative substitutions are where amino acids are replaced with amino acids of a different type. Broadly speaking, fewer non-conservative substitutions will be possible without altering the biological activity of the polypeptide. Suitably variants will be at least 60% identical, preferably at least 70%, even more preferably 80% or 85% and, especially preferred are 90%, 95% or 98% or more identity.

When comparing amino acid sequences for the purposes of determining the degree of identity, programs such as BEST-FIT and GAP (both from Wisconsin Genetics Computer Group (GCG) software package). BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention when discussing identity of sequences, the comparison is made by alignment of the sequences along their whole length.

The term "fragment thereof" refers to any portion of the given amino acid sequence which will form a complex with the similar activity to complexes including the complete α-lactalbumin amino acid sequence. Fragments may comprise more than one portion from within the full length protein, joined together. Portions will suitably comprise at least 5 and preferably at least 10 consecutive amino acids from the basic sequence.

Suitable fragments will be deletion mutants suitably comprise at least 20 amino acids, and more preferably at least 100 amino acids in length. They include small regions from the protein or combinations of these.

The region which forms the interface between the alpha and beta domains is, in human α-lactalbumin, defined by amino acids 34-38 and 82-86 in the structure. Thus suitable fragments will include these regions, and preferably the entire region from amino acid 34-86 of the native protein.

In a particularly preferred embodiment, the biologically active complex comprises a variant of α-lactalbumin in which the calcium binding site has been modified so that the affinity for calcium is reduced, or it is no longer functional.

It has been found that in bovine α-lactalbumin, the calcium binding site is coordinated by the residues K79, D82, D84, D87 and D88. Thus modification of this site or its equivalent in non-bovine α-lactalbumin, for example by removing one of more of the acidic residues, can reduce the affinity of the site for calcium, or eliminate the function completely and mutants of this type are a preferred aspect of the invention.

The $Ca^{2+}$-binding site of bovine α-lactalbumin consists of a $3_{10}$ helix and an α-helix with a short turn region separating the two helices (Acharya K. R., et al., (1991) *J Mol Biol* 221, 571-581). It is flanked by two disulfide bridges making this part of the molecule fairly inflexible. Five of the seven oxygen groups that co-ordinate the $Ca^{2+}$ are contributed by the side chain carboxylates of Asp82, 87 and 88 or carbonyl oxygen's of Lys79 and Asp84. Two water molecules supply the remaining two oxygen's (Acharya K. R., et al., (1991) *J Mol Biol* 221, 571-581).

Site directed mutagenesis of the aspartic acid at position 87 to alanine (D87A) has previously been shown to inactivate the strong calcium-binding site (Anderson P. J., et al., (1997) Biochemistry 36, 11648-11654) and the mutant proteins adopted the apo-conformation.

Therefore in a particular embodiment, the aspartic acid residue at amino acid position 87 within the bovine α-lactalbumin protein sequence is mutated to a non-acidic residue, and in particular a non-polar or uncharged polar side chain.

Non-polar side chains include alanine, glycine, valine, leucine, isoleucine, proline, phenylalanine, methionine, tryptophan or cysteine. A particularly preferred examples is alanine.

Uncharged polar side chains include asparagine, glutamine, serine, threonine or tyrosine.

In order to minimize the structural distortion in the mutant protein, D87 has also been replaced by an asparagine (N) (Permyakov S. E., et al., (2001) *Proteins Eng* 14, 785-789), which lacks the non-compensated negative charge of a carboxylate group, but has the same side chain volume and geometry. The mutant protein (D87N) was shown to bind calcium with low affinity ($K-_{ca}2\times10^5M^{-1}$) (Permyakov S. E., et al., (2001) *Proteins Eng* 14, 785-789). Such a mutant forms an element of the biologically active complex in a further preferred embodiment of the invention.

Thus particularly preferred variants for use in the complexes of the invention are D87A and D87N variants of α-lactalbumin, or fragments which include this mutation.

This region of the molecule differs between the bovine and the human proteins, in that one of the three basic amino acids (R70) is changed to S70 in bovine α-lactalbumin thus eliminating one co-ordinating side chain. It may be preferable therefore, that where the bovine α-lactalbumin is used in the complex of the invention, an S70R mutant is used.

The $Ca^{2+}$ binding site is 100% conserved in α-lactalbumin from different species (Acharya K. R., et al., (1991) *J Mol Biol* 221, 571-581), illustrating the importance of this function for the protein. It is co-ordinated by five different amino acids and two water molecules. The side chain carboxylate of D87 together with D88 initially dock the calcium ion into the cation-binding region, and form internal hydrogen bonds that stabilise the structure (Anderson P. J., et al., (1997) *Biochemistry* 36, 11648-11654). A loss of either D87 or D88 has been shown to impair Ca2+ binding, and to render the molecule stable in the partially unfolded state (Anderson P. J., et al., (1997) *Biochemistry* 36, 11648-11654).

Further, mutant proteins with two different point mutations in the calcium-binding site of bovine α-lactalbumin may be used. For example, substitution of the aspartic acid at position 87 by an alanine (D87A) has been found to totally abolish calcium binding and disrupt the tertiary structure of the protein. Substitution of the aspartic acid by asparagine, the protein (D87N) still bound calcium but with lower affinity and showed a loss of tertiary structure, although not as pronounced as for the D87A mutant (Permyakov S. E., et al., (2001) *Proteins Eng* 14, 785-789). The mutant protein showed a minimal change in packing volume as both amino acids have the same average volume of 125 $Å^3$, and the carboxylate side chain of asparagines allow the protein to co-ordinate calcium, but less efficiently (Permyakov S. E., et al., (2001) *Proteins Eng* 14, 785-789). Both mutant proteins were stable in the apo-conformation at physiologic temperatures but despite this conformational change they were biologically inactive. The results demonstrate that a conformational change to the apo-conformation alone is not sufficient to induce biological activity.

The structure of α-lactalbumin is known in the art, and the precise amino acid numbering of the residues referred to herein can be identified by reference to the structures shown for example in Anderson et al. supra. and Permyakov et al supra.

The medicaments produced in accordance with the invention are suitably pharmaceutical compositions in a form suitable for topical use, for example as creams, ointments, gels, or aqueous or oily solutions or suspensions. These may include the commonly known carriers, fillers and/or expedients, which are pharmaceutically acceptable.

Topical solutions or creams suitably contain an emulsifying agent for the protein complex together with a diluent or cream base. Such formulations can be applied directly to the papilloma.

The daily dose of the active compound varies and is dependant on the patient, the nature of the papilloma being treated etc. in accordance with normal clinical practice. As a general rule from 2 to 200 mg/dose of the biologically active complex is used for topical administration.

The applicants have carried out three studies on the effect of topical HAMLET treatment on papilloma in the form of cutanous papillomas of immunocompetent and immunosuppressed patients. The first study was performed as a double-blind, placebo-controlled investigation on 42 patients receiving either placebo solution (0.15M NaCl) or HAMLET (10 mg/ml, 0.7 mM in NaCl). One drop of substance was applied topically on the papilloma once a day for three weeks and the papillomas were measured and photographed once every week during the treatment period. Follow up visits were one and two months after completed treatment. All patients continued in a second open HAMLET study for a same period of time, and follow up was performed 1 month after completed treatment. A third open study was performed with 1.8 mM (25 mg/ml) HAMLET. Effective treatment was defined as a ≧75% reduction in papilloma volume.

As detailed below, in the placebo-controlled study HAMLET 0.7 mM (10 mg/ml) showed an effect (p<0.001) on 100% (20/20) of the patients (88/92 papillomas) that received HAMLET while 15% (3/20) of the patients (15/79 papillomas) receiving placebo showed effect. 45% (9/20) of the patients (19/92 papillomas) receiving HAMLET and 15% (3/20) of the patients (11/74 papillomas) receiving placebo had papillomas that disappeared totally during treatment or one month after treatment. In the second open HAMLET study an effect (p<0.001) was observed in 68% (23/34) of the patients. 29% (10/34) of the patients had papillomas (18/139) that disappeared totally during treatment or one month after treatment. In the third open study with 1.8 mM (25 mg/ml) HAMLET an effect (p<0.001) was observed in 70% (7/10) of the patients and in 66% (21/32) of their papillomas. 10% (1/10) of the patients had papillomas (1/32) that disappeared totally during treatment or one month after treatment. No adverse reactions were recorded.

To examine if the status of the immunesystem played a role in HAMLET treatment, immunocompetent and immunosuppressed (non-immunocompetent) patients were included in the study. There was no significant difference in response between these groups (p<0.001). Similarly, the effect of HAMLET was independent of gender of the patients.

Clearly then, HAMLET produced a highly beneficial therapy for papilloma.

In a further aspect of the invention, there is provided a method for treating papilloma which comprises administering to a patient in need thereof, a biologically active complex of α-lactalbumin, selected from HAMLET or a biologically active modification thereof, or a biologically active fragment of either of these.

Preferred examples of the biologically active complex are illustrated above. Preferably the biologically active complex is administered in the form of a topical composition, also as described above.

Materials and Methods

Preparation of Substance and Randomisation of Patients

Donors of breastmilk were non-smokers and were screened for HIV prior to preparation of HAMLET. Alpha-lactalbumin was purified from human milk whey by ammonium sulphate precipitation followed by phenyl-Sepharose chromatography and size-exclusion chromatography. Excess milk from the hospital milk bank was used according to regulations for administration to premature babies. HAMLET was generated from native α-lactalbumin on an oleic acid conditioned ion-exchange chromatography column, as described in the literature. The eluted fractions were dialysed against distilled water, lyophilised and stored at −20° C.

Furthermore, HAMLET was screened for bacterial contamination and was stored as dry substance in −20° C.

Patients

Patients with a history of recalcitrant papillomas were enrolled in a placebo-controlled study of topical HAMLET treatment. The majority was immuno-competent (n=31) and suffered no other illness. Eleven patients were immuno-suppressed after organ transplantation (n=7), systemic lupus erythematosus (n=1) or Sjorgens syndrome (n=1), and two had hypo-gamma-globulinemia. There were 27 females (64%) and 15 males (36%), with a median age of 22.5 years (range 6 to 60). Most lesions has not responded to salicylic acid or cryotherapy. Diagnosis was based on visual inspection by an experienced dermatologist. The included papillomas (n=173) were nodular or flat and localised on hands, lower arms of feet. Most patients had several lesions (median n=4, range 1 to 9).

Patients were randomised to the HAMLET or placebo group. The papillomas were inspected, measured and photographed at enrolment, weekly for three weeks and one month after completed treatment. A drop of HAMLET or placebo (0.15M NaCl) was applied topically on the lesion once a day and the lesion was covered with Comfeel® (Coloplast AB, Sweden) and Micropore tape (3M Health Care, Minn., U.S.A). Patients who cut or scratched the lesions during the treatment period were excluded from the analysis. The code was broken when all patients had completed the study.

Analysis

Groups were compared using the Student T test and the Chi 2 test.

Results:

HAMLET has Treatment Effect on Papilla

In the placebo controlled study, HAMLET had remarkable influence on the papillomas. Topical application of HAMLET was shown to significantly decrease the volume of skin papillomas as compared to the placebo control group. The effect was evaluated as the lowest recorded lesion volume within one month after the end of treatment. All the HAMLET treated patients showed a decrease in lesion volume, resulting in a median remaining volume of 14% (range 0-33%). A decrease by ≧75% was recorded in all HAMLET-treated patients (20/20 patients) and in 96% (88/92) of their lesions. Complete resolution of ≧1 lesion was recorded in 15% (3/20) of the patients, and in 21% of their lesions.

In contrast, no significant reduction in lesion volume was recorded in the placebo control group. The median remaining lesion volume was 81% (range 0-74%) and a decrease by ≧75% was recorded in 20% (15/74) of the lesions. Complete resolution of ≧1 lesion was observed in 15% (3/20) of the patients and 15% of the lesions (11/74).

The effect of HAMLET was independent of gender and immune status of the patients. The four immuno-suppressed patients who received HAMLET showed a significant decrease in lesion size (≧75%), and in three of them, at least one lesion disappeared. In contrast, the five immuno-suppressed patients in the placebo group showed no decrease in lesion size. HAMLET caused a significant reduction in all the females and males while complete resolution was observed in 8 of 14 females and in one of six males.

The effect of HAMLET was also independent of localisation and lesion characteristics. HAMLET treatment decreased the lesion volume by ≧75% in 96% (76/79) of the nodular lesions, and 24% (19/79) resolved. Similarly, HAMLET treatment reduced the volume in 92% (12/13) of the flat papillomas, but none resolved. The hand lesion volume decrease significantly in 97% (66/68) and 24% (16/68) of the lesions disappeared. Similarly, the foot lesions decreased in 92% (22/24) and 13% (3/24) of the lesions disappeared.

Additional Open Study

Ten new patients were recruited to an open study with the same protocol as described above. Five patients were immuno-competent and five were immunosuppressed. There were eight females (80%) and two males (20%), with a median age of 47 years (range 11 to 57). The included papillomas (n=32) were nodular (n=27) or flat and localised on hands (n=27) or feet. Most patients had several lesions (median n=3, range 1 to 7).

The effect of HAMLET was reproduced in this trial. The patients received 1.8 mM HAMLET. This caused a significant decrease in lesion volume in 7/10 patients and in 66% (21/32) of their lesions. In 10% (1/10) of the patients at least one lesion resolved completely comprising 3% of all lesions (1/32).

The invention claimed is:

1. A method for treating papilloma which comprises administering to a patient in need thereof, a biologically active complex of alpha-lactalbumin and a cis C18 unsaturated fatty acid cofactor which stabilizes the complex in a biologically active form, wherein alpha-lactalbumin is selected from the group consisting of:
   (i) an alpha-lactalbumin identified by SEQ ID NO:1, SEQ ID NO:2, SEQ ID NO:3, or SEQ ID NO:4,
   (ii) an alpha-lactalbumin comprising the region from amino acid 34-86 of human alpha-lactalbumin as identified by SEQ ID NO:1,
   (iii) an alpha-lactalbumin variant which has at least 95% identity to human alpha-lactalbumin as identified by SEQ ID NO:1, or has at least 95% identity to bovine alpha-lactalbumin as identified by SEQ ID NO:2, and wherein said variant has alpha-lactalbumin activity, and
   (iv) an alpha-lactalbumin variant identified by SEQ ID NO:5 or SEQ ID NO:6.

2. The method according to claim 1, wherein the cofactor is selected from a cis C18:1:9 or cis C18:1:11 unsaturated fatty acid.

3. The method according to claim 1, wherein the biologically active complex is obtainable either by isolation from casein fractions of milk which have been precipitated at pH 4.6, by a combination of anion exchange and gel chromatography, or by subjecting alpha-lactalbumin to ion exchange chromatography in the presence of a cis C18 unsaturated fatty acid cofactor from human milk casein.

4. The method according to claim 3, wherein the cofactor is selected from a cis C18:1:9 or a cis C18:1:11 unsaturated fatty acid.

5. The method according to claim 1, wherein the alpha-lactalbumin is an alpha-lactalbumin fragment comprising the region from amino acid 34-86 of human alpha-lactalbumin as identified by SEQ ID NO: 1.

6. The method according to claim 1, wherein the alpha-lactalbumin is an alpha-lactalbumin variant which has at least 95% identity to human alpha-lactalbumin as identified by SEQ ID NO:1, or has at least 95% identity to bovine alpha-lactalbumin as identified by SEQ ID NO:2, and wherein said variant has alpha-lactalbumin activity.

7. The method according to claim 6, wherein the cofactor is selected from a cis C18:1:9 or cis C18:1:11 unsaturated fatty acid.

8. The method according to claim 1, wherein the alpha-lactalbumin variant is identified by SEQ ID NO:5 or SEQ ID NO:6.

9. The method according to claim 8, wherein the cofactor is selected from a cis C18:1:9 or cis C18:1:11 unsaturated fatty acid.

10. The method according to claim 1, wherein the alpha-lactalbumin is an alpha-lactalbumin selected from the group of alpha-lactalbumin as identified as SEQ ID NO:1, SEQ ID NO:2, SEQ ID NO:3, or SEQ ID NO:4.

11. The method according to claim 10, wherein the alpha-lactalbumin is human or bovine alpha-lactalbumin as defined by SEQ ID NO:1 or SEQ ID NO:2.

12. The method according to claim 11, wherein the alpha-lactalbumin is human alpha-lactalbumin as identified by SEQ ID NO:1.

13. The method according to claim 10, wherein the cofactor is a cis C18:1 unsaturated fatty acid.

14. The method according to claim 10, wherein the cofactor is selected from a cis C18:1:9 or cis C18:1:11 unsaturated fatty acid.

15. The method according to claim 1, wherein the biologically active complex comprises human alpha-lactalbumin (SEQ ID NO:1) or a variant thereof which has at least 95% identity to human alpha-lactalbumin (SEQ ID NO:1) and a cis C18:1 unsaturated fatty acid, and wherein said variant has alpha-lactalbumin activity.

16. The method according to claim 15, wherein the cofactor is selected from a cis C18:1:9 or cis C18:1:11 unsaturated fatty acid.

* * * * *